US011517269B2

(12) United States Patent
Adams et al.

(10) Patent No.: US 11,517,269 B2
(45) Date of Patent: Dec. 6, 2022

(54) PROVIDING MONITORING SERVICES AND ACCESS TO INFORMATION TO CAREGIVERS, PATIENTS WITH IMPLANTED PRESSURE SENSORS, AND DISTRIBUTORS

(71) Applicant: Qura, Inc., Framingham, MA (US)

(72) Inventors: Douglas P. Adams, Sudbury, MA (US); Amitava Gupta, Roanoke, VA (US)

(73) Assignee: Qura, Inc., Duxbury, MA (US)

( * ) Notice: Subject to any disclaimer, the term of this patent is extended or adjusted under 35 U.S.C. 154(b) by 74 days.

(21) Appl. No.: 17/091,016

(22) Filed: Nov. 6, 2020

(65) Prior Publication Data

US 2021/0169427 A1    Jun. 10, 2021

Related U.S. Application Data

(63) Continuation of application No. PCT/US2018/050671, filed on Sep. 12, 2018.

(60) Provisional application No. 62/668,079, filed on May 7, 2018.

(51) Int. Cl.
| | |
|---|---|
| *G08B 1/08* | (2006.01) |
| *A61B 5/00* | (2006.01) |
| *G16H 10/60* | (2018.01) |
| *G16H 80/00* | (2018.01) |

(52) U.S. Cl.
CPC ............ *A61B 5/747* (2013.01); *A61B 5/6867* (2013.01); *G16H 10/60* (2018.01); *G16H 80/00* (2018.01); *A61B 2562/0247* (2013.01)

(58) Field of Classification Search
CPC ........ A61B 5/747; G16H 10/60; G16H 80/00; G16H 5/6867; G16H 2565/0247
USPC ................................................ 340/539.12
See application file for complete search history.

(56) References Cited

U.S. PATENT DOCUMENTS

| | | | |
|---|---|---|---|
| 8,475,374 B2 | 7/2013 | Irazoqui et al. | |
| 9,022,968 B2 | 5/2015 | Passaglia | |
| 9,078,613 B2 | 7/2015 | Irazoqui et al. | |
| 9,173,564 B2 | 11/2015 | Choo et al. | |
| 9,314,375 B1 | 4/2016 | Passaglia | |
| 9,369,459 B2 * | 6/2016 | Galwas | H04W 4/08 |
| 9,596,988 B2 | 3/2017 | Irazoqui et al. | |
| 9,662,021 B2 | 5/2017 | Chow et al. | |
| 10,044,227 B2 | 8/2018 | Chappell et al. | |
| 10,426,341 B2 | 10/2019 | Choo et al. | |

(Continued)

FOREIGN PATENT DOCUMENTS

| | | |
|---|---|---|
| JP | 2013158415 A | 8/2013 |
| WO | 2013090886 A1 | 6/2013 |

(Continued)

OTHER PUBLICATIONS

Hafezi et al., "An Ingestible Sensor for Measuring Medication Adherence." IEEE Transactions on Biomedical Engineering 62.1 (2015): 99. 11 pages.

(Continued)

*Primary Examiner* — Zhen Y Wu
(74) *Attorney, Agent, or Firm* — Smith Baluch LLP

(57) ABSTRACT

Methods based on providing monitoring services and access to information to caregivers, patients with implanted pressure sensors and distributors.

14 Claims, 3 Drawing Sheets

(56) References Cited

U.S. PATENT DOCUMENTS

| | | | |
|---|---|---|---|
| 2002/0077858 A1* | 6/2002 | Haines | G16H 40/67 705/3 |
| 2002/0198880 A1* | 12/2002 | Ullmann | G06F 16/2308 |
| 2003/0174066 A1* | 9/2003 | Goetz | A61N 1/37254 600/300 |
| 2005/0223008 A1* | 10/2005 | Kubota | G06F 21/6218 707/999.009 |
| 2006/0095958 A1* | 5/2006 | Lehinger | G06F 21/6245 726/6 |
| 2007/0061393 A1 | 3/2007 | Moore | |
| 2007/0162320 A1* | 7/2007 | Joshi | G06Q 10/10 713/166 |
| 2008/0139947 A1* | 6/2008 | O'Hanlon | G16H 10/20 707/999.107 |
| 2010/0137694 A1 | 6/2010 | Irazoqui et al. | |
| 2010/0309907 A1* | 12/2010 | Proulx | H04L 41/0816 370/389 |
| 2011/0040793 A1* | 2/2011 | Davidson | G06F 16/21 707/E17.005 |
| 2011/0273287 A1 | 11/2011 | LaLonde et al. | |
| 2013/0110540 A1* | 5/2013 | Kimberling | G16H 10/60 705/2 |
| 2014/0081667 A1* | 3/2014 | Joao | G16H 40/63 705/3 |
| 2014/0150074 A1* | 5/2014 | Galwas | H04L 63/065 726/5 |
| 2016/0196399 A1* | 7/2016 | Bonhomme | G16H 50/20 705/3 |
| 2017/0093619 A1* | 3/2017 | Chen | H04W 4/70 |
| 2017/0164831 A1 | 6/2017 | Choo et al. | |
| 2017/0209045 A1 | 7/2017 | Choo et al. | |
| 2018/0035888 A1 | 2/2018 | Irazoqui et al. | |
| 2018/0375382 A1 | 12/2018 | Chappell et al. | |
| 2019/0149318 A1* | 5/2019 | Abe | H04L 9/30 713/193 |
| 2019/0175015 A1 | 6/2019 | Adams et al. | |
| 2020/0237218 A1 | 7/2020 | Irazoqui et al. | |

FOREIGN PATENT DOCUMENTS

| | | |
|---|---|---|
| WO | 2019164940 A1 | 8/2019 |
| WO | 2019191748 A1 | 10/2019 |
| WO | 2020023036 A1 | 1/2020 |
| WO | 2020046299 A1 | 3/2020 |
| WO | 2020081072 A1 | 4/2020 |
| WO | 2020160262 A1 | 8/2020 |
| WO | 2020236139 A1 | 11/2020 |

OTHER PUBLICATIONS

International Search Report and Written Opinion in International Patent Application No. PCT/US2018/050671 dated Dec. 3, 2018, 14 pages.

* cited by examiner

PROVIDING MONITORING SERVICES AND ACCESS TO INFORMATION TO CAREGIVERS, PATIENTS WITH IMPLANTED PRESSURE SENSORS, AND DISTRIBUTORS

CROSS REFERENCE TO RELATED APPLICATIONS

This application is a bypass continuation of International Application No. PCT/US2018/050671, filed Sep. 12, 2018, which in turn claims priority to U.S. Provisional patent Application No. 62/668,079, filed May 7, 2018. Each of these applications is incorporated by reference herein in its entirety.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Wearable and implanted sensors that can monitor specific physiological parameters and wirelessly transmit such data to remote databases have proliferated over the last seven to ten years.

Implanted sensors are particularly useful in monitoring intraocular pressure in glaucoma patients, since elevated intraocular pressure (IOP) is the main risk factor for progression of glaucoma in both primary open angle glaucoma as well as angle closure glaucoma. Currently, IOP reduction remains the only treatment option for glaucoma, with options depending on many factors such as the type of glaucoma. Current monitoring of IOP occurs in the offices of a vision care practitioner, typically an ophthalmologist, ranging from once a year to once every 3-6 months, once glaucoma is diagnosed. It is known that IOP varies over a wide range in individuals, including a diurnal fluctuation, longer term variations and occurrence of spikes in IOP. A single measurement therefore cannot provide adequate data to diagnose an elevated IOP, which if measured, requires the prescription of pressure regulating or pressure reducing medication. Recognition that proper management of glaucoma requires regular measurement of IOP has led to development of implantable IOP sensors that can record IOP data several times a day, and transmit the data wirelessly to caregivers.

One of the oldest and most prolific wearable sensors is the Holter electrocardiogram (ECG) monitor, which has been in clinical use since the 1960s. The Holter monitor performs 24-hour ambulatory ECG recording for the purposes of capturing intermittent cardiac arrhythmias, which might otherwise be missed using standard assessment practices. Wearable sensors and implanted sensors generate data which satisfy the first three Vs of big data: volume, velocity and variety. The fourth V of veracity is also relevant to data from wearable and implanted sensors. The following categories of functions have been described for wearable sensors to detect falls among the elderly population: 1. manual emergency call; 2. automated detection of deviant behavior; 3. automated detection of falls; 4. automated detection of cardiac emergencies; and 5. handling potentially dangerous situations. Monitoring devices have been deployed at point of care locations to monitor patients' compliance with medical protocols for glaucoma patients who have to follow such protocols for decades. For example, Proteus Corporation recently tested an ingestible monitor to measure rate of compliance. (Robertson, T L, et al "An ingestible sensor for measuring medical adherence", in *IEEE Transactions in Biomedical Engineering*, 2015; 62, *pp* 99).

An embodiment of an exemplary sensor system 10 is shown in FIG. 1. System 10 is merely exemplary, and illustrates exemplary implant 12, exemplary remote interrogation device 14, application 16, and database 18. There are a wide variety of other implantable systems. Other implantable devices can have other components therein. Other external interrogating devices can have other components therein.

Deployment of an implanted or a wearable sensor requires development of a data handling system, which can include one or more of data collection, data clean-up, data storage, data transmission to a database, and data utilization. Design, development, deployment, and maintenance of the data handling system requires resources, and consequently there is a need for models that monetizes benefits to at least one of patients, payers and caregivers in order to provide funds for such development and/or maintenance of the system.

SUMMARY OF THE DISCLOSURE

The disclosure describes data handling systems for implanted intraocular pressure monitors, and models that monetize the benefits provided by such systems. The data handling systems can include or perform one or more of the following steps: receiving data from one or more implanted sensors, performing signal processing utilizing noise reduction algorithms and algorithms that introduce calibration methods and stored reference data for calibration to further process raw IOP data, data storage, uploading of data into a remote database, database design, and an interface with an electronic medical records ("EMR") database that is maintained by individual caregivers for each patient. The data handling systems and methods herein also describe methods of providing limited access to a remote database to an individual caregiver, which if desired the caregiver can use to set up an automated alerting system that may be customized for each patient. The systems and methods herein also make available data analytics, such as sorting data, performing trend analysis on selected patient populations, determining compliance by patient aggregates or subpopulations, efficacy of particular medications or MIGS as a function of prior disease status, estimating value by modeling improvement of visual acuity due to more efficacious treatment as a function of age, and estimating probable enhancement of quality of life as a function of treatment modalities taking into account available or published data on safety and efficacy of the treatment modalities. The systems and methods herein include at least three databases that interface in order to implement the methods and models described herein.

In an exemplary embodiment, the model comprises at least some of the following fees and costs: the price of the implant, the external package and the inserter; a fee (e.g., monthly, yearly) paid by the patient (or guardian of the patient) to have the EMR database utilized on behalf of the patient, which can include issuing alerts as required and agreed upon between the caregiver and the patient (alerts issued to medical emergency personnel, including paramedics, are currently paid for by the patient or by insurance coverage of the patient); a fee (e.g., monthly, yearly) charged to caregivers who have implanted the sensor or who have received access to one or more databases, in order to provide more efficacious and more efficient treatment; a lease payment made by pharmaceutical or medical device manufacturers who want to search the database(s) following rules of compliance to patient privacy rules issued by the government and/or the company. In some embodiments, not all of the fees need to be paid. For example, in some models, the patients may be paying fees but the caregivers may not. In other models the caregivers may pay a fee but the patients may not. There is some monetization based on a fee system, but not all fees must be paid by all of the different groups of individuals.

The models herein may be tested, verified, and validated prior to being deployed. Testing of the models includes presentation of the planned revenue generation approaches to key opinion leaders among the targeted professional customer base and recording their responses using a questionnaire. Testing also includes testing of the at least three databases, in particular various user interfaces that will guide and control access of the caregiver and EMR databases subscribed to by the caregiver to the remote database ("remote" database may also be referred to herein as a "second" database). The interfaces between the remote database and the EMR database and those between the remote database and a proprietary database (which may also be referred to herein as a "first" database) comprising proprietary algorithms for data analysis, recording accuracy and speed of data interchange, and the level of compliance to privacy and HIPPA regulations also require testing. The models are subsequently verified by launching it in a test market, and securing reimbursement to patients when appropriate from CMS (Center of Medicare and Medicaid Services) as well as private insurers. The models are finally validated by performing audits, performing simulations of data processing and data transfer using extreme and out of range parameters such as data volume generated by each sensor per day, number of caregivers and EMR databases seeking access simultaneously, reports of data analysis that may be beyond the capability of data analytics installed by the company, etc.

One aspect of the disclosure is a method of providing at least one of access to and services related to information related to pressures sensed by implanted medical sensors, and of monetizing the at least one of access to and services related to the information, comprising: providing a first database ("DB1") secured by first credentials so that it can be accessed only by one or more first individuals, the first individuals excluding a plurality of caregivers, wherein the first credentials, optionally login credentials, are only provided to the first individuals; providing a second database ("DB2") secured by second credentials so that it can be accessed only by the plurality of caregivers, but optionally also the first individuals, each of the plurality of caregivers being a caregiver of at least one of a plurality of patients that have been implanted with a medical pressure sensor, wherein the second credentials, optionally login credentials, are only provided to the plurality of caregivers and optionally to the first individuals, the DB2 having information stored thereon that is related to pressure that is sensed by each of a plurality of pressure sensors implanted in the plurality of patients, each of the plurality of pressure sensors having a unique identifier stored in DB2 so that the stored information is related to one of the unique identifiers and therefore to one of the plurality of implanted pressure sensors; providing a third database ("DB3") secured by third credentials so that it can be accessed by only one of the plurality of caregivers, wherein DB3 has stored thereon information related to pressure sensed by one or more of the plurality of pressure sensors, each of which is implanted in one of the plurality of patients and which is under the care of the one caregiver, wherein the access is limited by credentials only provided to the one caregiver, wherein DB1 is in unidirectional direct communication with DB2 such that DB1 at least partially populates DB2 with the information stored thereon, and either DB1 or DB2 is in direct communication with DB3 to at least partially populate DB3 with the information stored thereon, and wherein information stored on DB1 or generated by DB1 is synchronized to DB2 and DB3 at regular intervals, wherein a fee is charged to at least one of the following: the plurality of patients, in exchange for at least one of: one or more services related to the stored information, and access to the stored information, and the plurality of caregivers, in exchange for at least one of: one or more services related to the stored information, and access to the stored information.

DETAILED DESCRIPTION

The data handling system and methods herein can be used with any point of care intraocular pressure measurement system, including those designed for human use and those used in animals, especially household pets such as canines.

Figure 1:
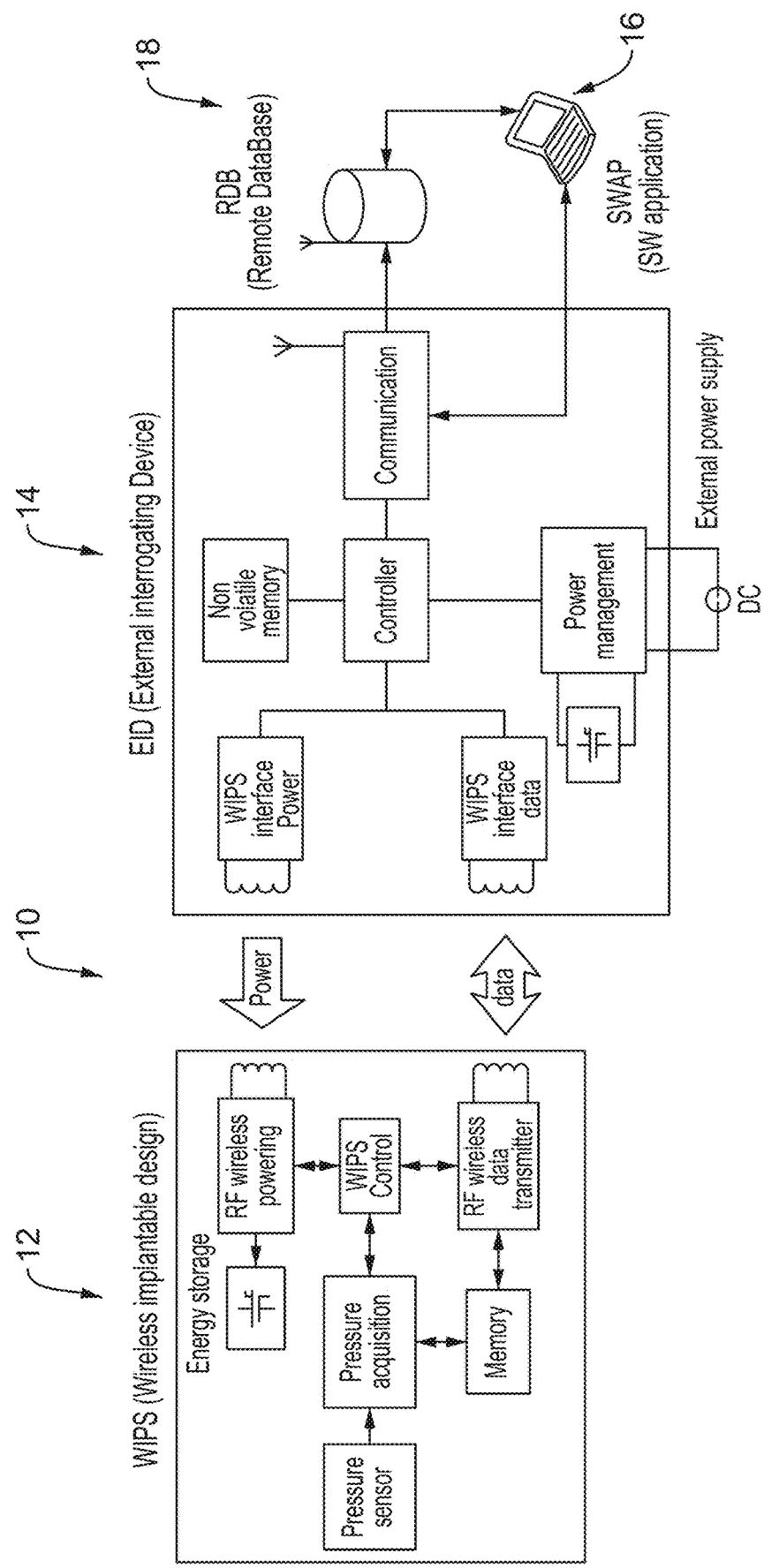
FIG. 1 is an exemplary system that includes an implantable device with a pressure sensor.

The intraocular pressure sensor systems herein (e.g., FIG. 1) include a pressure sensor device adapted to be implanted into the eye (i.e., the implant); an inserter to deliver the implant into the eye through a relatively small incision; an external unit that is adapted to be in wireless communication with the implant; and a remote database to accept and store data from the external unit. The external unit is also used to recharge the battery embedded in the sensor. The external unit is designed to be deployed at point of care locations, close to the patient. Any of data herein may be transferred by WIFI or Bluetooth, for example.

Raw data that is sensed by the sensor can be stored and/or processed to some extent in the implant and/or the external unit. For example, raw data can be stored in the implant (e.g., temporary storage), or it may be communicated to the external unit without storing it in the implant. The raw data may be processed to some extent in the implantable device and/or in the external unit, before it is communicated to the first database. The disclosure herein is not limited in how the raw data is processed or to what extent before it reaches the first database. And the first database can store a wide variety of information, including raw data or processed data, and information related to the raw data or processed data (e.g., timestamps of when pressure was sensed).

Figure 2A:
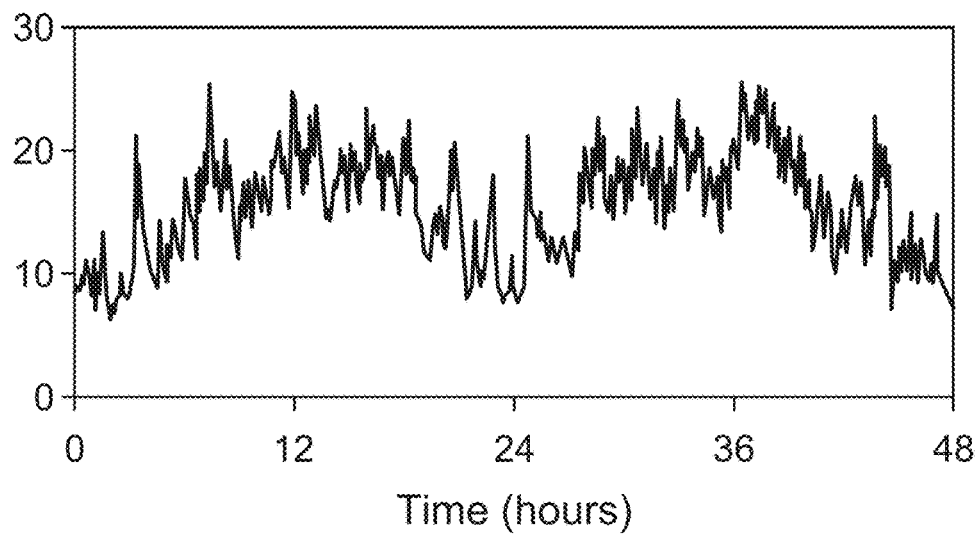
FIGS. 2A, 2B and 2C illustrate exemplary raw and processed intraocular pressure data.
Figure 2B:
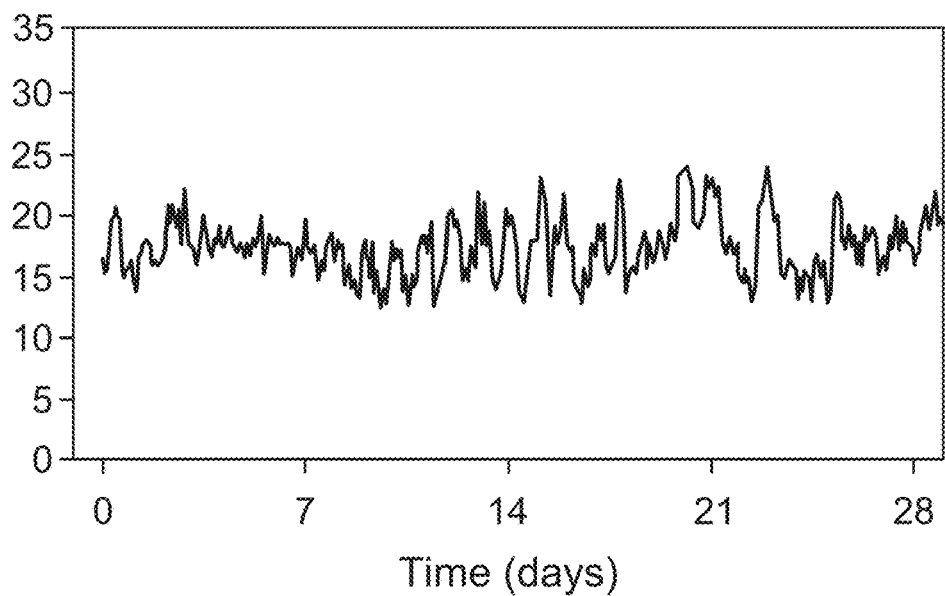
Figure 2C:
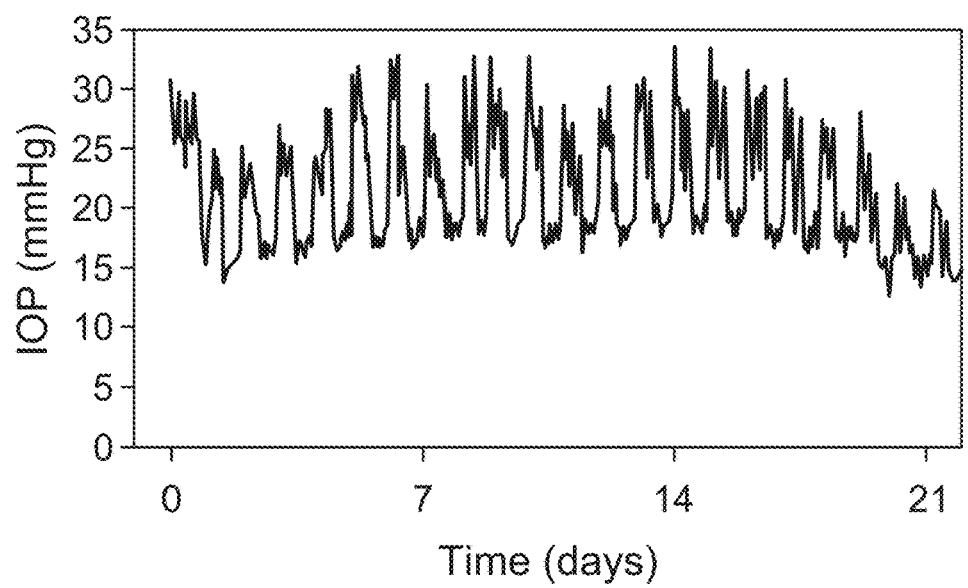

FIGS. 2A, 2B and 2C illustrate exemplary raw and smooth data on intraocular pressure measured on live conscious rats with an implanted intraocular pressure sensor. A first rat shows clear, diurnal variation in intraocular pressure (FIG. 2A), while the other does not (FIG. 2B). FIG. 2C shows smoothed data. The raw data generated by the sensors can be quite noisy, as can be seen in FIGS. 2A and 2B. Raw data may be smoothed by, for example, filtering it through a Kalman filter, by a band pass filter, or by taking running averages, as shown in FIG. 2C (also see U.S. Pat. Nos. 9,022,968 and 9,314,375, which are incorporated by reference herein).

The raw data may be voluminous, and if stored in the implant (for example), storing it in this form requires a sufficiently sized memory in the implant, as well as a rechargeable battery to provide power to the sensor electronics. One possibility is to apply embedded algorithms incorporated in the firmware of the implant electronics, and reduce the size of the data by averaging it or compressing it before storing it. In some embodiments, IOP data generated by a capacitative sensor can be stored in the RAM, processed, smoothed and filtered, then compressed using algorithms programmed in the flash memory of an ASIC, then stored in an EEPROM. The embedded algorithms can also include, for example, a calibration step of the electronic response.

In some exemplary embodiments, data processing and/or data compression can be mainly performed in an external unit (such as external unit 14 in FIG. 1), which can be tasked with both power and data management chores. Thus, in some embodiments, the raw data can be smoothed and averaged in the flash and random access memory of the implantable sensor, after which the data is transmitted to the external unit. The external unit can, for example, apply calibration routines, perform signal processing, including subtraction of the ambient atmospheric pressure recorded at the external unit at the same time when the intraocular pressure is recorded, filter the data, and perform trend analysis in order to identify missing data and other gross deviations from the trend.

In other embodiments, the sensor can be a passive sensor, comprising a wireless transceiver, and without an internal power source. In these embodiments, the data can be transferred to the external unit in terms of, as an example, frequency shift of a capacitative pressure sensor, and the change in resonance frequency is converted to an absolute magnitude of intraocular pressure. The raw data can then undergo signal processing, filtering and compression before being stored into the memory of an external unit. Atmospheric pressure can be recorded by the external unit at the same time, in order to calculate the difference between absolute intraocular pressure and atmospheric pressure. This difference is what is commonly referred to as intraocular pressure ("IOP"). Trend analysis and identification of missing data can also be performed in the external unit, before the data is uploaded into the remote database.

The data can be received wirelessly by the external unit, which can also be adapted to wirelessly reprogram one or more algorithms embedded in the FW of the ASIC in the implanted sensor. Preferably, the external unit is positioned close to the patient, for example a collar for a canine patient, or near the bedside of a patient's bed. The data can be further processed in the external unit, for example the multiple datasets taken throughout the day may be integrated to form a daily data profile without losing time stamp of each individual dataset. A trend analysis may also be performed at this stage. Daily data provide critical feedback to the caregiver on a patient who has recently undergone a surgical procedure or a change in their medical treatment protocol.

An external unit (e.g., external unit 14 in FIG. 1) can communicate information indicative of sensed information directly to a remote server, which can house one or more databases (e.g., database 18 shown in FIG. 1), such as cloud-based databases, or a database on a mobile device, such as a smartphone, tablet or other mobile device. In the latter instances, the mobile device can then upload the information to the remote database.

The remote database (e.g., the "first" database or the "second" database) may be deposited in a cloud based server, and may contain all the data obtained from all of the patients who have received a sensor implant. These data may be sorted, filtered and retrieved, upon request. The remote database can also be adapted to populate the electronic patient record of each caregiver who has a patient with an implanted sensor. The electronic medical records database ("EMR"; the "third" database herein) hosted by the caregiver receives data for each patient, and may be programmed to send alerts. The timing and content of these alerts may be customized for each patient and each caregiver.

The data received by the external unit can be transmitted via WIFI to a remote server, or a cloud based database on a regular basis, such as one, two, three, four, or five times a day. The database accepts the data and can archive it in a database that associates the data to data that already resides in the database with the patient's name or code, physiological characteristics such as age, sex, ethnicity, treatment history such as past surgeries, and history of medication protocols. The data received by the cloud based server can first be stored in a proprietary database (e.g., the "first" database as used herein) in which the data can be further analyzed using proprietary analytics, such as long term trend analysis, comparison with data of similar profile on other patients, and predictions of future progression of the disease based on such trend analysis utilizing neural networks and genetic algorithms. The data can then be transferred to a second database in the cloud based server along with a module that contains the results of data analysis performed in the first database. The first database is generally controlled and managed by the manufacturer, who is responsible for the accuracy of the database, and also responsible for controlling traffic and ensuring the fastest possible service for all subscribers, and fastest downloading of data to the EMR database (which is also referred to herein as a "third" database) maintained and controlled by a caregiver. The manufacturer generally develops the first database, and transfers control and operational responsibility of the EMR database to each caregiver who opts for this capability.

Data from the second database can be transferred to the third database that resides in a server controlled by the caregiver, where it is integrated with an electronic medical database ("EMR") maintained on each patient, containing the medical history of the patient. In some embodiments the second database may send the information to the third database. The third database can include an algorithm that has look up tables that is customized by the caregiver for each patient. In other words, the look up tables scan be customized both for each individual caregiver and for the individual patient. This look up table can be used by the one or more algorithms to issue alerts. Any number of alerts can be created depending on the need. Exemplary alerts include alerts to change medication protocol, alerts to go to an emergency facility, and alerts to schedule an appointment with the caregiver (e.g., for the following day). Alerts can be communicated via, for example, text messages sent to the patient or to the guardian of the patient (e.g., parent), and/or e-mails sent to the patient or the guardian of the patient. The expected outcome is that spikes in the patient's intraocular pressure are promptly detected, monitored, analyzed to be risky, and managed via alerts. As used herein, "patient" includes a guardian of the parent (e.g., relative).

The EMR database of the patient will continue to accumulate IOP data, along with trends and results of data analysis performed by algorithms deployed by the manufacturer as well a history of alerts issued, medical protocols prescribed, etc. This history supports development of long term disease management strategies, such as a decision to have surgical intervention, decision to implant a MIGS device, etc.

The disclosure above describes exemplary systems and infrastructure that allow patients and caregivers to have access to information and provide optional services (e.g., patient alerts) to manage a patient's medical conditions. To provide these benefits, the disclosure herein includes methods (which may also be referred to herein as models) that monetize the access and services.

In some embodiments, the methods and models include the costs associated with (e.g., the price) the implant, the external unit, and/or the inserter. This or these can be paid by the patient (including a guardian, or owner in the case where the patient is a canine or a household pet). In the case of humans, this can be entirely reimbursed by either CMS or private insurance coverage. Insurance coverage is available but not always common with household pet animals or other animals.

The methods and models can also include one or more fees (e.g., a monthly or yearly fee) paid by the patient in exchange for at least one of: more services related to the stored information, and access to the stored information. For example, the patient can pay a fee in exchange for having, for example, the EMR database utilized on behalf of the patient, or alerts issued as required and agreed upon between the caregiver and the patient. Alerts issued to medical emergency personnel, including paramedics, are currently paid for by the patient or by insurance coverage of the patient.

The methods and models can also include one or more fees (e.g., a monthly or yearly fee) paid by the caregiver of a patient with an implanted sensor. The fee(s) can be paid in exchange for at least one of: one or more services related to the stored information, and access to the stored information. The access and/or services can provide more efficacious and more efficient treatment by the caregiver.

The methods and models can also include a fee (e.g., lease payment) made by pharmaceutical or medical device manufacturers who want to search the database(s), remaining compliant to patient privacy rules issued by the government and/or the company.

Table 1 illustrates merely exemplary ranges of fees that can be sources of revenue for any of the methods herein.

Each of the exemplary four sources of revenue in Table 1 provides an excellent value proposition to the customer, caregiver and the industry. For example, the implant will significantly prolong retention of functional vision among the elderly, leading to an enhancement of their quality of life and life expectancy. For example, implantation can prevent falls that are a leading cause of death and loss of mobility, which shortens life expectancy. The fee to be paid by the patient enables the patient or guardian to, for example, receive alerts when needed and protects the patient from sudden loss of vision, due to a spike in their IOP. The monthly fee to be paid by the caregiver can provide, for example, access and automatic downloading of patient IOP data into their electronic medical record. This makes it possible to apply for reimbursement without the need for additional documentation, which provides ready access to the patient's IOP history and company generated analytics that identify trends that will support accurate diagnosis. These analytics can be developed by consultation with experts and glaucoma specialists not affiliated with the company, in order to receive objective guidance.

Leasing of access to the database to pharmaceutical and device manufacturers can transform best practice in glaucoma therapy. For example, post market surveillance often required by the FDA and CMS as a part of the drug approval process will become much easier, saving the manufacturers substantial expenses. The manufacturers will be allowed to run their proprietary analytics on the sorted database and maintain confidentiality from the company, so that their proprietary information and trade secrets are protected. Access to efficacy and safety performance may be achieved by monitoring data on patients immediately upon deployment.

Exemplary costs to a company performing any of the methods herein are given in Table 2, such as design, development and testing of databases and data interfaces and user interfaces. Here costs include amortization of capital required for manufacture, and non-recurring engineering costs.

TABLE 1

| Source of Revenue | One Time Typical, Range | Monthly: Typical, Range | Yearly: Typical, Range |
| --- | --- | --- | --- |
| Implant package | $900 $500-$3000 | NA | NA |
| Monthly fee to be paid by patient | NA | $25 $15-120 | $300 $180-$1,440 |
| Monthly fee to be paid by caregiver | NA | $50 $0-$250 | $600 $0-$3,000 |
| Lease to be paid by pharmaceutical or device manufacturers | $50,000 $10,000-$10,000,000 | $50,000 $5,000-$100,000 | $600,000 $60,000-$1,200,000 |

TABLE 2

| Item | Cost of development (Typical, range) | Cost per unit (Typical, range) | Monthly Maintenance cost (Typical, range) |
|---|---|---|---|
| Implant | $5MM ($2MM-$25MM) | $50 ($30-$150) | NA |
| External Unit | $1MM ($0.5MM-$2MM) | $25 ($20-$100) | Replacement at no charge, if found defective |
| Inserter | $0.5MM ($250,000-$1MM) | $15 ($10-$50) | NA |
| FW in sensor | $0.5MM ($0.25MM-$0.75MM) | NA | |
| FW in External unit | $0.5MM ($0.25MM-$0.75MM) | NA | |
| Proprietary Database | $1.5MM ($0.75-3.0MM) | | $1,500 ($1000-$5,000) |
| Remote Database | $2.5MM ($1.0MM-$3.0MM) | | $2,500 ($1,500-$5,000) includes lease costs |
| EMR Database, including interface with remote database and alerts | $1.5MM ($1.0MM-$4.0MM) | | $100 ($50-$150) |
| Signal processing algorithms | $1.0MM ($0.75MM-$1.5MM) | NA | $500 |
| Data Analytics | $2.0MM ($1.5MM-$5MM) | NA | $10,000 |

Testing of the models can include presentation of the planned revenue generation approaches with key opinion leaders among the targeted professional customer base and recording their responses using a questionnaire. Testing can also include testing of the three databases, in particular various user interfaces that will guide and control access of the caregiver and EMR databases subscribed to by the caregiver to the remote database. The interfaces between the remote database (the "second" database) and the EMR database (the "third" database) and that between the remote database and the proprietary database (the "first" database) can comprise proprietary algorithms for data analysis, recording accuracy and speed of data interchange, and the level of compliance to privacy and HIPPA regulations. The issuance of alerts, if implemented, is generally also tested, for example, when pressure value exceeds a certain value or threshold, or when the data recorded exceeds or falls below a limit value (indicating hypotony) on two consecutive occasions. The issuance of an alert may also be made coincidental with issuance of a command that goes back to the point of care system whereby the sensor begins recording data at more frequent intervals.

The models can be subsequently verified by launching it in a test market, and securing reimbursement to patients when appropriate from Center of Medicare and Medicaid Services ("CMS") as well as private insurers.

The models can be finally validated by performing audits, performing simulations of data processing and data transfer using extreme and out of range parameters such as data volume generated by the sensor per day, number of caregivers and EMR databases seeking access simultaneously, reports of data analysis that may be beyond the capability of data analytics installed by the company, etc.

An exemplary database for processing, storage and applications of the data is the SQL server based database provided by Microsoft Azure®. The Azure based SQL server can accept both unorganized and streaming data, so that it can provide a location for the proprietary database in which the APPS include data analytics.

Another exemplary database is the Amazon Aurora, a MySQL and PostgreSQL compatible relational database built for the cloud. According to the Amazon website, Aurora is up to five times faster than standard MySQL databases and three times faster than standard PostgreSQL databases. Aurora is fully managed by Amazon Relational Database Service, which automates administration tasks like hardware provisioning, database setup, patching, and backups. Aurora features a distributed, fault-tolerant, self-healing storage system that auto-scales up to 64 TB per database instance. Aurora delivers high performance and availability with up to 15 low-latency read replicas, point-in-time recovery, continuous backup to Amazon S3, and replication across three Availability Zones. Other databases can of course be used with systems and methods described herein.

A "caregiver," as that term is used herein, can refer to any of the following: an ophthalmologist, an ophthalmic surgeon, a glaucoma specialist, a surgeon specializing in cataract surgery or a combined procedure, a surgeon specializing in refractive surgery, an optometrist, an nurse or an attending physician at an urgent care facility, or anyone on a medical team of any of those listed above, for example. A caregiver is not necessarily limited to those listed above, however, and may include other types of people, if they are someone other than the patient in which the implanted sensor is implanted.

All state of the art approaches to database security can be implemented as a part of an overall security strategy, including use of automated random 16 character password generators, and data encryption, always before data is transferred from one database into another. Security will be routinely given higher priority than speed of data transfer. Accuracy of the data transfer process will be audited on a regular basis, and data transfer process will be duplicated when transferring data at random intervals, so that the two sets of downloaded data can be matched against one another, and in case of a mismatch, the data transfer process will be repeated a third time, in order to resolve the mismatches by only accepting data that has been matched at least once. Transfer of algorithms or code from any database can include a cut out, in which the code is checked for malware.

Figure 3:
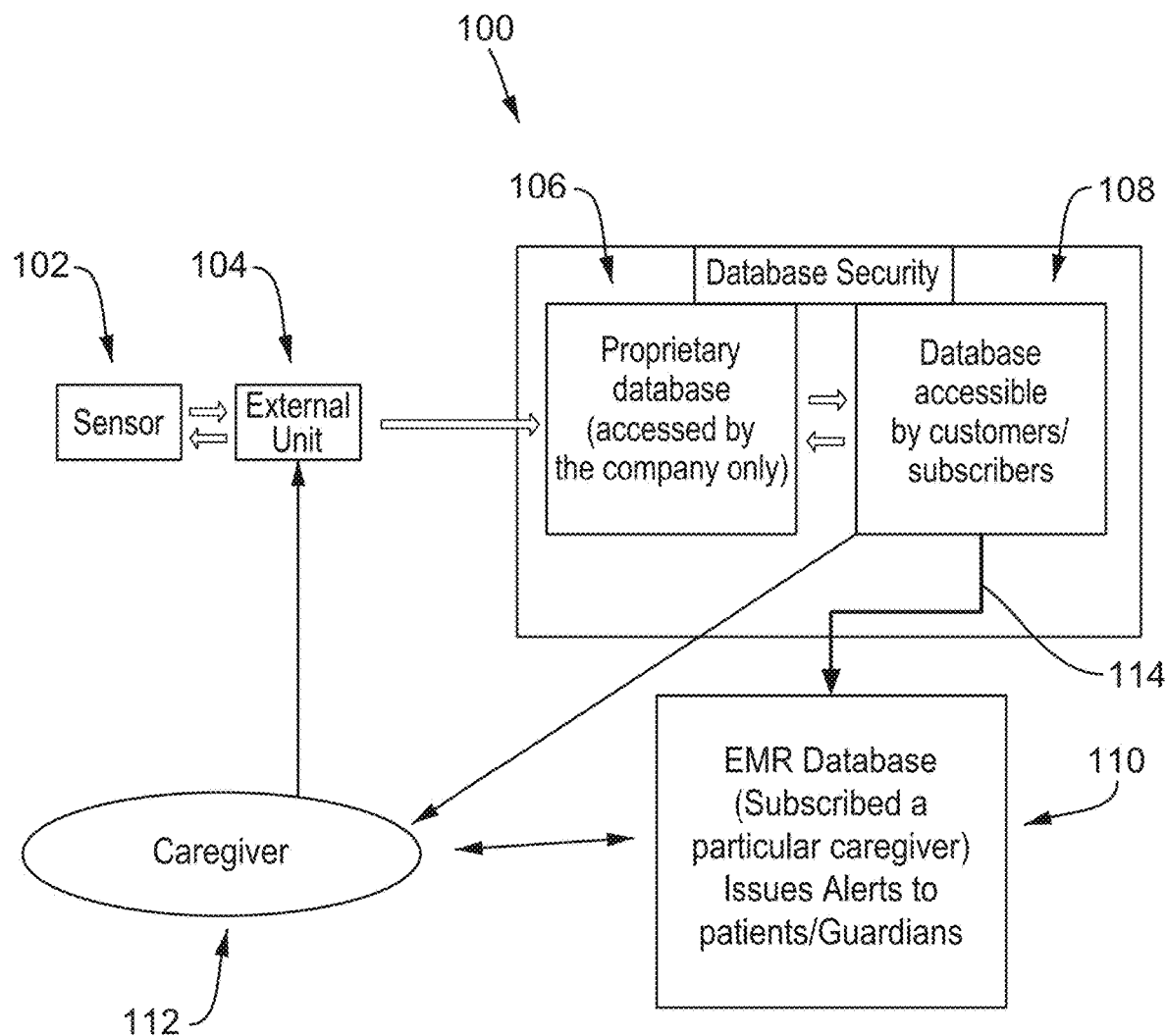
FIG. 3 is an exemplary system that be used for any of the methods herein.

FIG. 3 illustrates an exemplary infrastructure that can utilize any of the methods herein. System 100 includes implant 102, which includes a pressure sensor. System 100 also includes external unit 104. System 100 includes first proprietary database 106, second database 108, and third database 110. Caregiver 112 is also illustrated to illustrate exemplary involvement in the system. In this example, there is unidirectional communication between caregiver 112 and external unit 104, bidirectional communication between caregiver 112 and third database 110, unidirectional communication between second database 108 and caregiver 112 and bidirectional communication between first database 106 and second database 108, as shown by the arrows in FIG. 3. In this exemplary embodiment, the data and/or information provided to third database 110 is communicated from second database 108, but could come partially or fully from first database 106. Simulation of data and code transfer can be carried out using actually deployed databases, by using test codes and altered data to test the ability of the system to correct those errors automatically. Patients' names and contact information will always be coded, and the code will be archived in a separate database that is stored in a local device with back up, but not on the internet.

Exemplary data and/or information that can be stored in first database 106 includes, for example, IOP with or without time stamp, the patient's name and/or other demographic information, patient identification indicator, patient medication details, and details of past treatments, maintenance data, error log, etc. Exemplary operations that can be performed on the first database include performing a sanity check of IOP value, analyzing maintenance data and error log, big data analytics (e.g., machine learning), and extracting relevant parameters for large-scale clinical studies.

Exemplary data and/or information that can be stored in third database 110 includes, for example, IOP with time stamp for all patients managed by the caregiver, the patient's name and/or other demographic information, data analytics, and alerts, which can be customized for each patient and caregiver.

ADDITIONAL EXAMPLES

1. A database system with no less than three separate databases, comprising: a first database adapted to accept data from a point of care system and perform data processing utilizing algorithms to identify trends and level of compliance of the patient to a prescribed medical protocol, a second database that includes an archive of intraocular pressure data on a plurality of patients and that complies with HIPPA regulations, and a third database that comprises the electronic medical record of at least a single patient, wherein said third database is adapted to issue alerts to the patient and/or the caregiver of the patient, indicating the type of emergency medical condition identified by the third database.

2. The system of example 1, wherein the first database comprises data related to intraocular pressure recorded on a plurality of patients, received from point of care systems deployed near each of the plurality of patient, archives such data, and performs algorithms that are adapted for pattern recognition and/or trend analysis and interface with and transmit data to the second remote database.

3. The system of example 1, wherein the second database comprises interfaces with the first and third databases, has a user interface for the use of customers, and delivers data on one or more patients to a customer authorized to receive data on said patients.

4. The system of example 1, wherein the third database is integrated with electronic medical record of a particular patient under care of a specific caregiver who receives access to the third database, wherein said third database is adapted to issue an alert to at least one of the patient and the caregiver upon fulfillment of certain trends or other features selected by the caregiver for issuance of the alert.

5. The system of example 1, wherein the point of care system has a non-volatile memory to store data received from a sensor in the point of care system, signal processing and noise filtering algorithms, and a mechanism to reprogram the sensor, including its frequency of operation.

6. The system of example 1, wherein the second database is adapted to be accessed to provide data analytics of patient subpopulations at a specific disease state, or under a specific medical protocol, or implanted with a specific MIGS device, or a combination of such conditions, performed on the first database.

7. A method of monetizing the first, second and third databases in example 1, wherein a fee per patient is charged to a caregiver who is a caregiver to a patient with an implanted sensor.

8. The method of example 7, wherein the fee is $1.00 to $50.00, such as $5.00 to $50.00, such as $15.00 to $40.00, per month.

9. A method of monetizing the first, second and third databases in example 1, wherein a fee is charged to each patient or the guardian of the patient implanted with a sensor.

10. The method of example 9, wherein the fee is $15.00 to $120.00, such as $20.00 to $50.00, per month.

11. A method of monetizing the first, second and third databases in example 1, wherein a charge, optionally a leasing charge, is applied to a manufacturer of a pharmaceutical or a device, wherein the device or pharmaceutical has been used to treat a patient implanted with a sensor, wherein the manufacturer seeks IOP data and analysis thereof relevant to determination of safety and/or efficacy and/or long term reliability of the device or pharmaceutical upon routine clinical use.

The invention claimed is:

1. A method of providing at least one of access to and services related to information related to pressures sensed by implanted medical sensors, and of monetizing the at least one of access to and services related to the information, comprising:

providing a first database ("DB1") secured by first credentials so that DB1 can be accessed only by one or more first individuals, the one or more first individuals excluding a plurality of caregivers, wherein the first credentials are only provided to the one or more first individuals;

providing a second database ("DB2") secured by second credentials so that DB2 can be accessed only by the one or more first individuals and at least one of the plurality of caregivers each of the plurality of caregivers being a caregiver of at least one of a plurality of patients that have been implanted with a medical pressure sensor, wherein the second credentials are only provided to the one or more first individuals and at least one of the plurality of caregivers DB2 having first information stored thereon that is related to pressure that is sensed by at least one pressure sensor of a plurality of pressure sensors implanted in at least one patient of the plurality of patients, each pressure sensor of the plurality of pressure sensors having a unique identifier stored in DB2 so that the first information is related to at least one unique identifier and therefore to the at least one pressure sensor of the plurality of pressure sensors;

providing a third database ("DB3") secured by third credentials so that DB3 can be accessed by only one caregiver of the plurality of caregivers, wherein DB3 has second information stored thereon related to pressure sensed by one or more of the plurality of pressure sensors, each of which is implanted in one of the plurality of patients and which is under care of the only one caregiver of the plurality of caregivers, wherein DB1 is in unidirectional direct communication with DB2 such that DB1 at least partially populates DB2 with the first information, and either DB1 or DB2 is in direct communication with DB3 to at least partially populate DB3 with the second information, and wherein third information stored on DB1 or generated by DB1 is synchronized to DB2 and DB3 at regular intervals, wherein a fee is charged to at least one of the following:
  the plurality of patients, in exchange for at least one of: one or more services related to at least one of the first information or the second information, and access to at least one of the first information or the second information, or
  the plurality of caregivers, in exchange for at least one of: one or more services related to at least one of the first information or the second information, and access to at least one of the first information or the second information.

2. The method of claim 1, wherein the fee is paid by the plurality of patients and the plurality of caregivers.

3. The method of claim 2, wherein the fee paid by the plurality of caregivers is greater than the fee paid by the plurality of patients.

4. The method of claim 1, wherein the fee is charged to the plurality of patients in exchange for at least one or more services, the one or more services including an alert to at least one of the patients of the plurality of patients or a caregiver of a patient of the plurality of patients, the caregiver of the patient being one of the plurality of caregivers.

5. The method of claim 1, wherein an additional fee is charged to a pharmaceutical or medical device company in exchange for access to at least one of the first information or the second information while complying with patient privacy rules.

6. The method of claim 1, wherein access to DB2 is limited such that one caregiver of the plurality of caregivers can only access information stored therein related to a pressure sensor that has been implanted in one patient of the plurality of patients that is under care of the one caregiver of the plurality of caregivers.

7. The method of claim 6, wherein one or more of the plurality of caregivers is given access to information in DB2 related to sensor data from one pressure sensor of the plurality of pressure sensors that is implanted in one patient of the plurality of patients that is not under the care of the one or more of the plurality of caregivers.

8. The method of claim 1, wherein DB1 has stored thereon one or more proprietary algorithms accessible only by the one or more first individuals, the one or more proprietary algorithms adapted to process sensed data or information indicative of the sensed data.

9. The method of claim 1, wherein at least one of the first credentials or the second credentials comprise login credentials.

10. A plurality of databases for providing access to and services related to information related to pressures sensed by implanted medical sensors, comprising:
  a first database ("DB1") secured by first credentials so that DB1 can be accessed only by one or more first individuals, the one or more first individuals excluding a plurality of caregivers, wherein the first credentials are only provided to the one or more first individuals;
  a second database ("DB2") secured by second credentials so that DB2 can be accessed only by the one or more first individuals and at least one of the plurality of caregivers each of the plurality of caregivers being a caregiver of at least one of a plurality of patients that have been implanted with a medical pressure sensor, wherein the second credentials, are only provided to the the one or more first individuals and at least one of the plurality of caregivers, DB2 having first information that is related to pressure that is sensed by at least one pressure sensor of a plurality of pressure sensors implanted in at least one patient of the plurality of patients, each pressure sensor of the plurality of pressure sensors having a unique identifier stored in DB2 so that the first information is related to at least one unique identifier and therefore to at least one pressure sensor of the plurality of pressure sensors;
  a third database ("DB3") secured by third credentials so that DB3 can be accessed by only one caregiver of the plurality of caregivers, wherein DB3 has second information stored thereon related to pressure sensed by one or more of the plurality of pressure sensors, each of which is implanted in one of the plurality of patients and which is under care of the only one caregiver of the plurality of caregivers, and
  wherein DB1 is in unidirectional direct communication with DB2 such that DB1 at least partially populates DB2 with the first information, and either DB1 or DB2 is in direct communication with DB3 to at least partially populate DB3 with the second information,
  wherein third information stored on DB1 or generated by DB1 is synchronized to DB2 and DB3 at regular intervals.

11. The plurality of databases of claim 10, wherein access to DB2 is limited such that one caregiver of the plurality of caregivers can only access first information therein related to a pressure sensor of the plurality of pressure sensors that has been implanted in one patient of the plurality of patients that is under care of the one caregiver of the plurality of caregivers.

12. The plurality of databases of claim 11, wherein one or more of the plurality of caregivers is given access to first information in DB2 related to sensor data from one pressure sensor of the plurality of pressure sensors that is implanted in one patient of the plurality of patients that is not under the care of the one or more of the plurality of caregivers.

13. The plurality of databases of claim 10, wherein DB1 has stored thereon one or more proprietary algorithms accessible only by the one or more first individuals, the one or more proprietary algorithms adapted to process sensed data or information indicative of the sensed data.

14. The plurality of databases of claim 10, wherein at least one of the first credentials or the second credentials comprise login credentials.

* * * * *